US011151722B2

(12) United States Patent
Duchesne et al.

(10) Patent No.: US 11,151,722 B2
(45) Date of Patent: Oct. 19, 2021

(54) SYSTEM AND METHOD FOR ESTIMATING SYNTHETIC QUANTITATIVE HEALTH VALUES FROM MEDICAL IMAGES

(71) Applicants: UNIVERSITÉ LAVAL, Quebec (CA); MCGILL UNIVERSITY, Montreal (CA)

(72) Inventors: Simon Duchesne, Quebec (CA); Pierre Gravel, Quebec (CA); Louis Collins, St-Lambert (CA)

( * ) Notice: Subject to any disclaimer, the term of this patent is extended or adjusted under 35 U.S.C. 154(b) by 170 days.

(21) Appl. No.: 16/317,596

(22) PCT Filed: Jul. 22, 2016

(86) PCT No.: PCT/CA2016/050871
§ 371 (c)(1),
(2) Date: Jan. 14, 2019

(87) PCT Pub. No.: WO2018/014108
PCT Pub. Date: Jan. 25, 2018

(65) Prior Publication Data
US 2019/0287247 A1 Sep. 19, 2019

(51) Int. Cl.
*G06T 7/00* (2017.01)
*G06T 7/143* (2017.01)
(Continued)

(52) U.S. Cl.
CPC .......... *G06T 7/0016* (2013.01); *A61B 5/0042* (2013.01); *A61B 5/055* (2013.01);
(Continued)

(58) Field of Classification Search
None
See application file for complete search history.

(56) References Cited

U.S. PATENT DOCUMENTS

| 2008/0080768 A1 | 4/2008 | Li et al. |
| 2012/0053447 A1 | 3/2012 | Duchesne |

(Continued)

OTHER PUBLICATIONS

Lerch, Jason P., et al. "Automated cortical thickness measurements from MRI can accurately separate Alzheimer's patients from normal elderly controls." Neurobiology of aging 29.1 (2008): 23-30. (Year: 2008).*

(Continued)

*Primary Examiner* — Samah A Beg
(74) *Attorney, Agent, or Firm* — Anglehart et al.

(57) ABSTRACT

A computer-implemented method, an apparatus, and a system for estimating synthetic values of quantitative metrics are provided. They involve calculating new, more accurate boundaries using a classifier based on local intensity and spatial estimators, for the segmentation mask provided by a non-local means patch-based segmentation in a test image, and estimating for the pixels of interest at least one synthetic value of a quantitative metric using a given value of the quantitative metric assigned to the reference images and the boundaries. The method, apparatus, and system provide the advantage of generating synthetic values directly comparable against known values for given subjects or against predetermined scales for diagnostic or prognostic purposes. In the specific case of Alzheimer's disease, the invention stretches the predictive range up to two full decades, which constitutes a significant advance in the field of medical diagnostics.

20 Claims, 7 Drawing Sheets

(51) Int. Cl.
    *G06T 7/13*      (2017.01)
    *G06T 7/174*     (2017.01)
    *G16H 30/40*     (2018.01)
    *A61B 5/00*      (2006.01)
    *A61B 5/055*     (2006.01)
    *G06K 9/46*      (2006.01)
    *G06K 9/62*      (2006.01)
    *G06T 7/12*      (2017.01)

(52) U.S. Cl.
    CPC ............ *G06K 9/4604* (2013.01); *G06K 9/623* (2013.01); *G06K 9/6269* (2013.01); *G06T 7/0014* (2013.01); *G06T 7/12* (2017.01); *G06T 7/13* (2017.01); *G06T 7/143* (2017.01); *G06T 7/174* (2017.01); *G16H 30/40* (2018.01); *A61B 2576/026* (2013.01); *G06K 9/6256* (2013.01); *G06K 2209/051* (2013.01); *G06T 2207/10088* (2013.01); *G06T 2207/20081* (2013.01); *G06T 2207/20161* (2013.01); *G06T 2207/30016* (2013.01)

(56) References Cited

U.S. PATENT DOCUMENTS

2012/0093381 A1\* 4/2012 Fan .................. G06T 7/143
                                                      382/131
2014/0226882 A1\* 8/2014 Collins ............... G06T 7/0012
                                                      382/128

OTHER PUBLICATIONS

EP16909074.3 supplementary European search report dated Jan. 13, 2020.
Jongkreangkrai et al., "Computer-aided classification of Alzheimer's disease based on support vector machine with combination of cerebral image features in MRI", Journal of Physics: Conference Series, vol. 694, No. 1, 1 to 38.
PCT/CA2016/050871 IPRP.
PCT/CA2016/050871 ISR.
PCT/CA2016/050871 search strategy.
Related European application No. 16909074.3 Examination report dated Feb. 25, 2021.

\* cited by examiner

SYSTEM AND METHOD FOR ESTIMATING SYNTHETIC QUANTITATIVE HEALTH VALUES FROM MEDICAL IMAGES

TECHNICAL FIELD

The present invention relates generally to medical image processing. More specifically, the invention relates to methods, apparatuses, and systems for determining synthetic health values from medical images.

BACKGROUND

In many fields of medical study related to diagnostic or prognostic there is a need to obtain information related to the health status of a specific tissue, lesion, organ, or function, in the least invasive way possible. This is not always achievable, for example in organs such as the brain. Biopsies, as minimally invasive as they can become, are the main tool employed in many fields of medicine, yet remain difficult to perform, require surgical approaches and specialized expertise, can bring about complications, and are overall costly. Further, biopsies do not always provide the right type or a complete set of information regarding health status.

Medical imaging, on the other hand, holds vast promises to achieve similar aim, provided there are systems, methods and techniques proposed that can optimize and extract the right information value from the images obtained of the living tissue, lesion, organ or function.

As an example of this problem, the field of early detection in Alzheimer's disease constitutes a good, but by no means sole, example. Early detection is critical for the successful treatment of of Alzheimer's disease (AD) and constitutes a high priority research area. Diagnostic accuracy of baseline clinical testing for AD averages 78% (22% error rate), and this, with insufficient diagnostic specificity. The most recent solutions for improving diagnostic accuracy and specificity involve combining core (clinical/cognitive) and supportive (neuroimaging/genetic/proteomic) assessment techniques.

As a supportive assessment technique, structural neuroimaging typically involves analyzing structural magnetic resonance imaging (MRI), which can provide in vivo, non-invasive assessment of global, regional, and local cerebral morphology changes due to AD such as tissue atrophy. It has therefore been proposed as a quantitative biomarker of disease progression. Hippocampal atrophy in particular, as measured automatically via MRI, has been correlated with confirmatory AD pathological findings. The most validated procedure to estimate atrophy is to calculate volumes with manual outlining using anatomical landmarks by an expert rater on high resolution T1-weighted MRI. Results of studies in different laboratories consistently show 15 to 40% hippocampal tissue loss in probable AD vs. controls (CTRL).

Beyond the hippocampus, a recent and growing body of literature has used machine learning methods to extract high-dimensional MRI features from regions of interest, on which classification functions are built to assist in clinical diagnostic of probable AD, with accuracies reaching 92% in some cases. The patch-based technique described in US. Pat. Pub. No. 20140226882 A1 presents some of the best predictive results so far, with 75% accuracy on average, seven years before diagnostic.

The patch-based technique consists in labelling each voxel within a small zone of a new image (the "patch") by comparing its surroundings with similar information from images of training individuals, for which the clinical status is known. Grading is done by computing the weighted average of all grades from the template images whose patches are used to segment the target image.

SUMMARY

The segmentation and grading information that is generated by US. Pat. Pub. No. 20140226882 A1, while useful, presents with limitations which are addressed in the current invention.

The first is related to the accuracy of the segmentation. It has been found that the boundary of segmented objects tends to be unreliable. Importantly, this boundary can severely affect the accuracy of the segmentation of co-located structures (e.g. the hippocampus and the amygdala); impact the total number of voxels present in a structure (e.g. a one-voxel difference in surface of the hippocampus can mean a >40% difference in volume); and thus severely skew the grading result. Related to this issue is the use of the patch-based technique to segment multiple labels at a time, covering a larger field of interest. In that case there needs to be a means to co-segment the labels at the junctions between structures.

The third issue is related to the grading information. While achieving a diagnostic probability, such as demonstrated in US. Pat. Pub. No. 20140226882 A1, is useful, and seems to be related to clinical evaluations (e.g. as demonstrated by correlation with MMSE), it remains that in a large number of cases, and for a large number of other medical questions, obtaining quantitative, immediately comparable health metrics would be equally, if not more useful. Examples include obtaining a synthetic estimate of brain "age", which can be directly compared to chronological age, and adds value to the image process. This has the benefit of being completely open ended, normally distributed, and can be used to track with high sensitivity the results of interventions. Another example includes the ability of obtaining synthetic values, in vivo, of the extent of the deposition of various proteins in AD. At present these could only be obtained ex vivo, after autopsy, when pathology reports on these depositions using scales such as that of Braak et al. [Braak, H., et al., *Staging of Alzheimer disease-associated neurofibrillary pathology using paraffin sections and immunocytochemistry*. Acta neuropathologica, 2006. 112(4): p. 389-404.], or Thal et al. [Thal, D. R., et al., *Phases of A beta-deposition in the human brain and its relevance for the development of AD*. Neurology, 2002. 58(12): p. 1791-800.]. Having such information in vivo would be extremely useful, as a means of performing a non-invasive, digital biopsy. Other examples will be provided below.

a) Accuracy of Segmentations

The Applicant has found that in a computer-implemented method for processing medical images comprising the step of calculating in a processor a classification function comparing the distribution of parameters for a given patch on the boundary of a structure of interest in a test image with the parameters of the same patch on the boundary of a structure of interest in a number of reference images, the step of classifying the patch and assigning the proper label to the voxel at the center of the patch as belonging to the most probable structure of interest, including a means to decide on the best structure in the case of multiple structures statistically or probabilistically being possible in the voxel of interest, with the advantage of bringing greater accuracy to the task of segmenting the structure of interest. In the specific case of the hippocampus, the present invention increases the correlation with validation standards.

According to one embodiment of the present invention, there is provided a computer-implemented method for processing medical images, the method comprising the step of calculating in a processor a classification function comparing the distribution of parameters for a given patch on the boundary of a structure of interest in a test image with the parameters of the same patch on the boundary of a structure of interest in a number of reference images, the step of classifying the patch and assigning the proper label to the voxel at the center of the patch as belonging to the most probable structure of interest, including a means to decide on the best structure in the case of multiple structures statistically or probabilistically being possible in the voxel of interest, with the advantage of bringing greater accuracy to the task of segmenting the structure of interest.

The Applicant has found that in an apparatus for processing medical images comprising the step of calculating in a processor a classification function comparing the distribution of parameters for a given patch on the boundary of a structure of interest in a test image with the parameters of the same patch on the boundary of a structure of interest in a number of reference images, the step of classifying the patch and assigning the proper label to the voxel at the center of the patch as belonging to the most probable structure of interest, including a means to decide on the best structure in the case of multiple structures statistically or probabilistically being possible in the voxel of interest, with the advantage of bringing greater accuracy to the task of segmenting the structure of interest. In the specific case of the hippocampus, the present invention increases the correlation with validation standards.

According to another embodiment of the present invention, there is provided an apparatus for processing medical images, the method comprising the step of calculating in a processor a classification function comparing the distribution of parameters for a given patch on the boundary of a structure of interest in a test image with the parameters of the same patch on the boundary of a structure of interest in a number of reference images, the step of classifying the patch and assigning the proper label to the voxel at the center of the patch as belonging to the most probable structure of interest, including a means to decide on the best structure in the case of multiple structures statistically or probabilistically being possible in the voxel of interest, with the advantage of bringing greater accuracy to the task of segmenting the structure of interest.

The Applicant has found that in a system for processing medical images comprising a medical imager configured to generate a test image, the integration of an apparatus configured to classify voxels based on said parameters and of assigning voxels based on said means provides the advantage of increasing the accuracy of the segmentation of co-located structures (e.g. the hippocampus and the amygdala); impact the total number of voxels present in a structure (e.g. a one-voxel difference in surface of the hippocampus can mean a >40% difference in volume); and thus helps to improve the grading result.

The Applicant has found found that in an apparatus for processing medical images comprising a medical imager configured to generate a test image, the integration of an apparatus configured to classify voxels based on said parameters and of assigning voxels based on said means provides the advantage of increasing the accuracy of the segmentation of co-located structures (e.g. the hippocampus and the amygdala); impact the total number of voxels present in a structure (e.g. a one-voxel difference in surface of the hippocampus can mean a >40% difference in volume); and thus helps to improve the grading result.

According to another embodiment of the present invention, there is provided an apparatus for processing medical images, the method comprising a medical imager configured to generate a test image, a network system to access multiple reference images, the integration of an apparatus configured to perform patch-based initial classification of voxels into structures, the integration of an apparatus configured to classify voxels based on parameters and of assigning voxels to structures of interest.

b) Estimating Synthetic Values:

The Applicant has found that in a computer-implemented method for processing medical images, the steps of calculating in a processor classifier-driven boundaries on a segmentation mask in a test image and estimating in a processor for pixels of interest of the test image at least one synthetic value of a quantitative metric using a given value of the quantitative metric assigned to reference images and the boundaries provide the advantage of generating a synthetic value directly comparable against the actual value for the given subject or against predetermined scales for diagnostic or prognostic purposes. In the specific case of AD, the present invention stretches the predictive range up to two full decades prior to clinical diagnosis, which constitutes a significant advance in the field of medical diagnostics.

According to a another embodiment of the present invention, there is provided a computer-implemented method for processing medical images, the method comprising calculating in a processor classifier-driven boundaries on a segmentation mask in a test image and estimating in a processor for pixels of interest of the test image at least one synthetic value of a quantitative metric using a given value of the quantitative metric assigned to reference images and the boundaries.

The Applicant has found that in an apparatus for processing medical images, a calculator configured to calculate classifier-driven boundaries on a segmentation mask in a test image and a quantitative metric calculator configured to estimate for pixels of interest of the test image at least one synthetic value of a quantitative metric using a given value of the quantitative metric assigned to reference images and the boundaries provide the advantage of generating a synthetic value directly comparable against the actual value for the given subject or against predetermined scales for diagnostic or prognostic purposes. In the specific case of AD, the present invention stretches the predictive range up to two full decades prior to diagnosis, which constitutes a significant advance in the field of medical diagnostics.

According to a another embodiment of the present invention, there is provided an apparatus for processing medical images comprising a calculator configured to calculate classifier-driven boundaries on a segmentation mask in a test image and a quantitative metric calculator configured to estimate for pixels of interest of the test image at least one synthetic value of a quantitative metric using a given value of the quantitative metric assigned to reference images and the boundaries.

The Applicant has found that in a system for processing medical images comprising a medical imager configured to generate a test image, the integration of an apparatus configured to generate an overall synthetic value for the test image and of a client application configured to receive and present the overall synthetic value provides the advantage of generating a synthetic value directly comparable against a known value for the given subject or against predetermined scales for diagnostic or prognostic purposes. In the specific case of AD, the present invention stretches the predictive range to two full decades, which constitutes a significant advance in the field of medical diagnostics.

According to another embodiment of the present invention, there is provided a system for processing medical images comprising a medical imager configured to generate a test image, an apparatus configured to generate an overall synthetic value for the test image, and a client application configured to receive and present the overall synthetic value, wherein the imager, apparatus and client application communicate data over a network and return to the client application the overall synthetic value. The apparatus comprises a calculator configured to calculate classifier-driven boundaries on a segmentation mask in a test image, a quantitative metric calculator configured to estimate for pixels of interest of the test image at least one synthetic value of a quantitative metric using a given value of the quantitative metric assigned to reference images and the boundaries, and a quantitative metric aggregator configured to calculate the overall synthetic value for the test image from the at least one synthetic value.

BRIEF DESCRIPTION OF THE DRAWINGS

The invention will be better understood by way of the following detailed description of embodiments of the invention with reference to the appended drawings, in which.

DETAILED DESCRIPTION

The present invention relates generally to medical image processing. More specifically, the invention relates to methods, apparatuses, and systems for determining synthetic health values from medical images.

Figure 1:
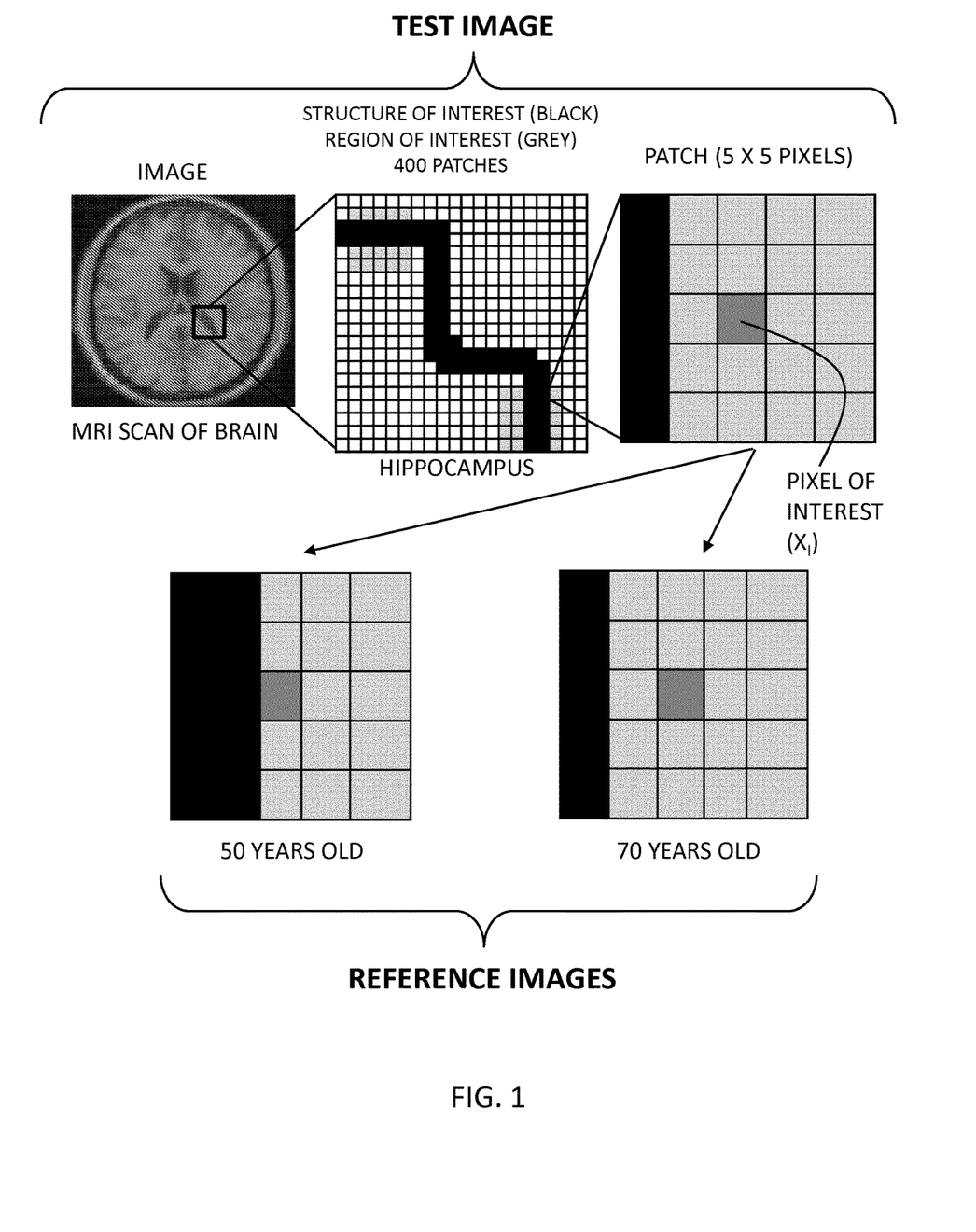
FIG. 1 is a highly schematic drawing of the method of the present invention.

FIG. 1 is a highly schematic drawing of the method of the present invention. An image acquisition system acquires a test image (see top left of FIG. 1), in this case, an MRI scan of a test subject's brain. The test subject or the doctor wants information from scan data relating to specific brain structures such as the hippocampus (see top middle of FIG. 1) that are indicative or biomarkers for mild cognitive impairment (MCI) and AD. The area shown on the scan is presented for illustrative purposes and is not actually the hippocampus (HC). The area blown up is shown as a 20×20 square of 400 patches where the HC is shown in black and two square regions of interest (ROI) are highlighted in grey. One patch (see top middle of FIG. 1) is further blown up to the pixel level as a 5×5 square representative of a volume of 5×5×5 voxels. The computer-implemented method of the present invention identifies patches within the ROI to compare them with many (or in some case only with the most related) patches taken from healthy subjects of different ages, exemplified by a first patch taken from a 50-year-old subject (see bottom left of FIG. 1) and a second patch taken from a 70-year-old subject (see bottom right of FIG. 1). An adapted version of the Buades nonlocal means estimator provides for determining whether the portion of the HC identified in the ROI resembles more that of a healthy 50-year-old subject, a healthy 70-year-old subject, or healthy subjects of other ages on the basis of reference images taken from a reference image library that covers a wide range of ages. In the example shown in FIG. 1, it is clear that the test subject's patch bears a greater resemblance to the 70-year-old subject's patch. If the test subject is significantly younger, the resemblance may suggest that the test image HC has atrophied as a consequence of MCI or AD. It is important to note that FIG. 1 is highly simplified. For example, it should be understood that all pixels of an ROI can be segmented and/or graded and not just the central pixel of a patch. In other words, each patch is centered on a pixel but patches centered on successive pixels overlap one another. It will also be appreciated that each age is not represented by a single patch, but rather by an ensemble of patches where weightings/states determine the result.

In Coupé et al. [Coupé, P., Manjon, J. V., Fonov, V., Pruessner, J., Robles, M., Collins, D. L., 2010. Nonlocal patch-based label fusion for hippocampus segmentation. Med Image Comput Assist Interv 13, 129-136.], the nonlocal means estimator was introduced in the context of segmentation by averaging labels instead of intensities. By using a training library of N subjects whose segmentations of structures are known, the weighted label fusion is estimated as follows:

$$v(x_i) = \frac{\sum_{s=1}^{N} \sum_{j \in \Omega} w(x_i, x_{s,j}) \cdot l(x_{s,j})}{\sum_{s=1}^{N} \sum_{j \in \Omega} w(x_i, x_{s,j})} \quad (3)$$

where $l(x_{s,j})$ is the label (i.e., 0 for background and 1 for structure) given by the expert to the voxel $x_{s,j}$ at location j in training subject s. With a label set of $\{0,1\}$ voxels with value $v(x_i) \geq 0.5$ are considered as belonging to the considered structure and the remaining voxels as background. In Coupé et al, the authors showed that accurate segmentations of anatomical structures can be obtained using this simple patch-based label fusion framework. We will refer to this segmentation as the original patch-based segmentation.

In the current invention, the applicants are the first to introduce the use of local intensity-based refinement of label segmentation using a classifier. The current embodiment uses support vector machine (SVM), but other embodiments could use different classifiers, such as graph cuts.

The SVM classifier is used to reassign voxel classes (or re-label voxels). For each voxel k that needs to be classified, a vector of predictors of length N is assigned. In this embodiment, an 8-dimensional vector is assigned:

$$X_k = [\mu_k, \sigma_k, \bar{\mu}_k^3, \bar{\mu}_k^4, \bar{\mu}_k^5, |\nabla I|_k, \nabla^2 I_k, \nabla_\sigma^2 I_k] \quad (4)$$

where $\mu_k$ and $\sigma_k$ are the local mean and standard deviation of the intensity in a neighbourhood centered at the voxel, here set at 3×3×3 but which could be of a different size, and which could be anisotropic. The next components are a variety of local metrics within the neighbourhood. This could comprise moments, operators, textures, bags of intensities, or other well-known metrics for the art. In this embodiment a set of three components are the normalized, central moments (NCM) of the probability distribution function (PDF) of intensities:

$$\tilde{\mu}_k^n = \frac{1}{27}\sum_{i=1}^{27}\left(\frac{I_i - \mu_k}{\sigma_k}\right)^n \qquad (5)$$

where the $I_i$ are the voxel intensities in the same cubic neighbourhood. Another component is the norm of the local intensity gradient. It is computed by convolving the image with an operator (for example edge operators). In this embodiment the 3×3×3 Sobel operator is used to evaluate each of the partial derivatives, from which the norm of the local gradient is computed. Two other components are from kernels, in this embodiment the 3×3×3 Laplacian kernel and the 7×7×7 Laplacian of a Gaussian kernel with a standard deviation of 40 mm. Other kernels with other dimensions and standard deviations can be used. It has been found that the best choice of predictors is a combination of those related to the local intensity PDF the spatial intensity distribution (local slope and curvature at different scales).

The initial class of the voxel k, assigned by the patch-based technique is the observation $Y_k$ that corresponds to the vector of predictors $X_k$ (see Eq. 4). Combining the data from all the N voxels in the mask defined by the original patch-based segmentation and its outer shell, for example the hippocampus, an N×8 observation matrix X and N×1 column vector Y are obtained. A coarse Gaussian classifier is applied to this (X, Y) dataset, using cross validation to minimize the rate of misclassification of the new predicted vector Y'. The updated mask can be recreated using the Y' vector that holds the new class of each one of the N voxels.

From local intensity-based refinement to post-processing of the SVM a posteriori map. For each voxel, the SVM classifier provides the a posteriori probability that the voxel belongs to class 1. Thus a 3D probability map is generated, which is subsequently smoothed using a procedure based on a penalized least squares method and the discrete cosine transform. This method provides a robust 3D smoothing. The new mask voxels are found by thresholding above 50% the smoothed a posteriori 3D probability map generated by the SVM classifier. Only the largest segmented connected object is kept in order to remove remaining binary noise and disconnected components, which are generally much smaller than the region of interest. Removing fragments of the segmented region in coarse resolution images can generate false negatives. However, one should keep in mind that the experts generated continuous segmentations for most features. Overall, the new segmentation mask should be composed of voxels from only one object, bar small inclusions of different tissues (e.g. lesions within brain; different tumor regions). In the example of the hippocampus, these are small clumps of CSF found beside 75% of the HC in the reference segmentations; 95% of them were smaller than 37 mm$^3$ (i.e. 37 voxels). After the patch segmentation, 95% of the remaining clumps were smaller than 5 mm$^3$. After using the SVM classifier, only 1% of the HC were still found associated with CSF and 95% of the clumps were smaller than 4 mm$^3$. Hence, keeping only the largest segmented object for a given label has minimal consequences given the volumes of the features of interest.

From post-processing of the SVM a posteriori map to combining multiple a posteriori maps. The refining step involving the SVM classifier is repeated for every label to segment in the test image. The assignment of labels based on the smoothed probability maps, that extend beyond their original patch masks and thus overlap their neighbouring masks, must be done with great care. Bayes theorem is used to sort out each voxel class:

$$C_k = \arg_C \max\{p(X_k|C)N_C\} \qquad (6)$$

where $p(X_k|C)$ is the (smoothed) a posteriori probability that the voxel k belongs to class C, and $N_C$ is the number of voxels involved in the corresponding SVM classification. Implementation of the class sorting is then performed by generating a map of the product $p(X_k|C)N_c$ for each label processed and then compared, for each voxel, to the maximum value of the maps generated for the previous labels. The voxels for which the maximum change are assigned the new label. The steps presented herein above yield classifier-driven boundaries that can be used for grading purposes as explained herein below.

According to one embodiment of the present invention, the refining step involving the SVM classifier is repeated for all structures and the resulting a posteriori maps are consolidated to arrive at a pixel classification that is more likely to reflect reality than one derived from a posteriori maps generated for a subset of structures.

It is important to note that while the classifier-driven boundaries are described as calculated using the steps presented herein above, they may alternatively be calculated using other combinations of image processing steps. For instance, while the classifier-driven boundaries are described as calculated on segmentation masks generated using the patch-based technique, they can alternatively be calculated on segmentation masks generated using other techniques.

From segmentation to grading. For each patch of the subject under study, a comparison is performed with all the patches constituting the selected training subjects. This way, the simultaneous segmentation and grading of the studied structure is obtained. The final grading value, or structure-based synthetic value, corresponds to the average value over the estimated segmentation. This procedure is achieved for each studied structure, such as left and right HC, and left and right entorhinal complex (EC). This is similar to the procedure in US. Pat. Pub. No. 20140226882 A1.

From grading to calculating an overall synthetic value. Applicants extend this segmentation method to efficiently aggregate a quantitative brain health metric in order to estimate the proximity (in the nonlocal means sense) of each voxel compared to the populations constituting the training library.

It will be appreciated that in the specification, the term "quantitative metric" refers to any semi-quantitative or fully quantitative metric deemed pertinent for the purposes of determining a state of health of a test subject. Semi-quantitative metrics are scales that follow abnormal distributions. They include clinical scales such as the Geriatric Depression Scale (GDS), neuropsychological scales such as those associated with the MMSE and the Montreal Cognitive Assessment (MoCA), as well as pathological scales such as those associated with Braak, Thal, and the Consortium to Establish a Registry for Alzheimer's Disease (CERAD). Conversely, fully quantitative metrics are scales that follow a standard distribution, such as age and blood cholesterol levels.

Several strategies can be used to fuse the average grading of studied structures. First, if there are two structures, each structure can be used separately. Second, it is possible to assign the same weight to both structures. In this embodiment, the left and right HC and entorhinal cortices (e.g., $\bar{g}_{HC}=(\bar{g}_{HC\_left}+\bar{g}_{HC\_right})/2$). This strategy of fusing both sides appears to be more robust to segmentation inaccuracy when compared to Chupin et al. [Chupin, M., Gerardin, E., Cuingnet, R., Boutet, C., Lemieux, L., Lehericy, S., Benali, H., Garnero, L., Colliot, O., 2009a. Fully automatic hippocampus segmentation and classification in Alzheimer's disease and mild cognitive impairment applied on data from ADNI. Hippocampus 19, 579-587]. During experiments, applicants found that these two strategies provided similar results for HC and EC. However, for the HC-EC complex, the best strategy was to compute left and right average grading values over HC-EC segmentation (thus giving more importance to HC because of its larger size) and then to use the mean of both sides ($\bar{g}_{HCEC}=(\bar{g}_{HCEC\_left}+\bar{g}_{HCEC\_right})/2$). In some embodiments, the overall synthetic value is the mean value of all synthetic values estimated for the pixels of interest. However, in other embodiments, the overall synthetic value is calculated in a different manner. For instance, in some embodiments, a structure-specific synthetic value is calculated for each studied structure, and the overall synthetic value is calculated as the weighted average of the structure-specific synthetic values, wherein at least some of the structure-specific synthetic values are assigned different weights as a function of the relative importance given to the underlying structures.

Figure 2:
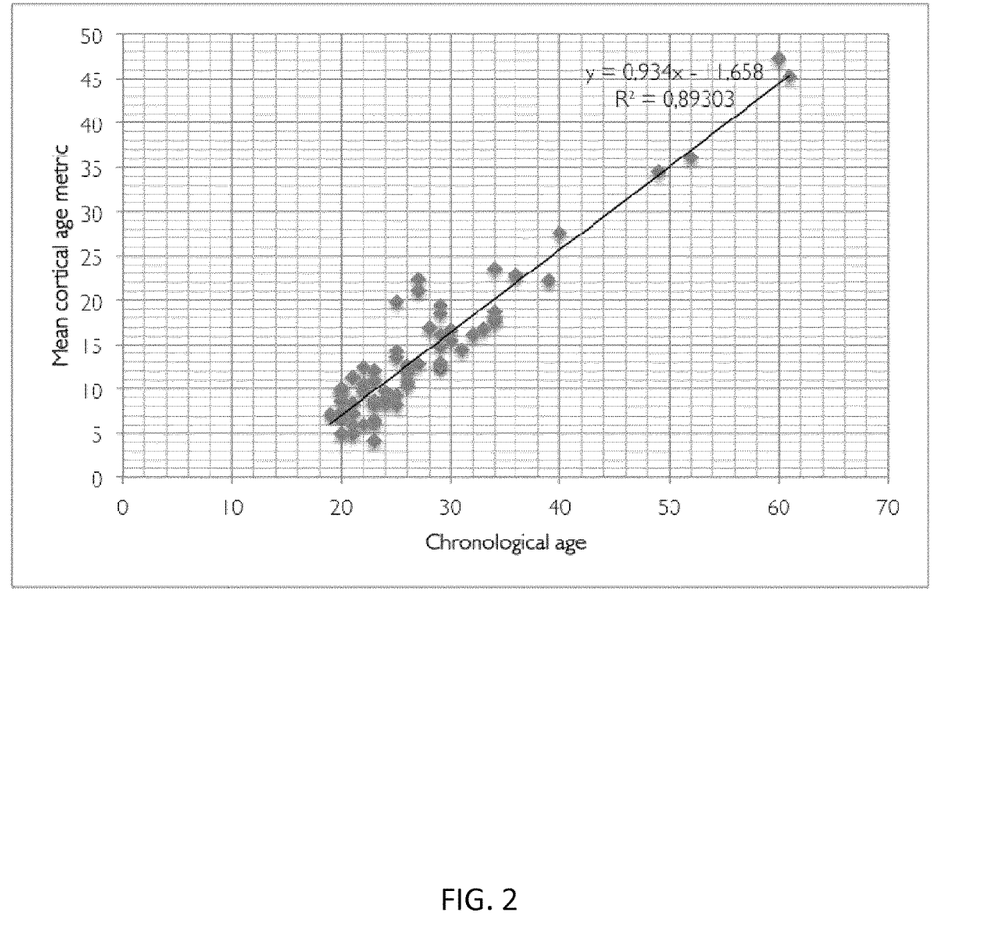
FIG. 2 is a graph showing estimated cortical ages as a function of chronological ages.

Experiment confirming the present invention's ability to estimate synthetic values for quantitative metrics. The experiment consisted in using the method to estimate synthetic values of a specific, quantitative health metric: the cortical age of a brain from an MRI. For the purposes of the experiment, 101 semi-automated cortical labels provided in the MindBoggle dataset (Klein 2012) and included in the Freesurfer software were used. These labels come from individuals aged 19 to 61 years old. Using the method of the present invention, the Applicant segmented each cortical area in a leave-one-out fashion, calculated a cortical area age for each cortical area, and calculated a brain age as the mean of all cortical area ages. Preliminary data on 67 randomly chosen individuals out of the 101 in the MindBoggle are shown in FIG. 2. Strikingly, the technique provides a synthetic brain age estimate, which is extremely well correlated ($r^2=0.89$) with chronological age.

Interpreting the overall synthetic value to determine a state of health. In some embodiments, the overall synthetic value is compared against a classification scale specific to the quantitative metric in order to determine a state of health of the structure under study. For instance, if the quantitative metric is the Braak scale score, the overall synthetic value corresponds to a Braak scale score calculated by comparing an image of a test subject's brain against images of reference subjects' brains, the reference subjects having known Braak scale scores from post-mortem examinations. The overall synthetic value can then be directly used to classify the severity of disease cognitive impairment.

In other embodiments, the overall synthetic value can be compared against a known value to assess the difference, or delta, between the values, for the test subject, and subsequently compare the difference assessed for the test subject against differences assessed for reference subjects presenting different health profiles. For instance, if the quantitative metric is the cortical age of a brain, the overall synthetic value corresponds to an age calculated by comparing an image of a test subject's brain against images of reference subjects' brains, the reference subjects having known chronological ages. The calculated brain age can be compared against the chronological age of the test subject to assess the difference therebetween. The difference is subsequently compared against differences assessed for AD, MCI, and CTRL reference subjects of the same chronological age. If the difference assessed for the test subject is closer to the differences assessed for AD reference subjects of the same age, the state of health of the test subject would reflect a likelihood of AD. In another example, the difference could be used to assess the relative effect of an intervention aimed to reduce this synthetic age discrepancy.

Figure 3:
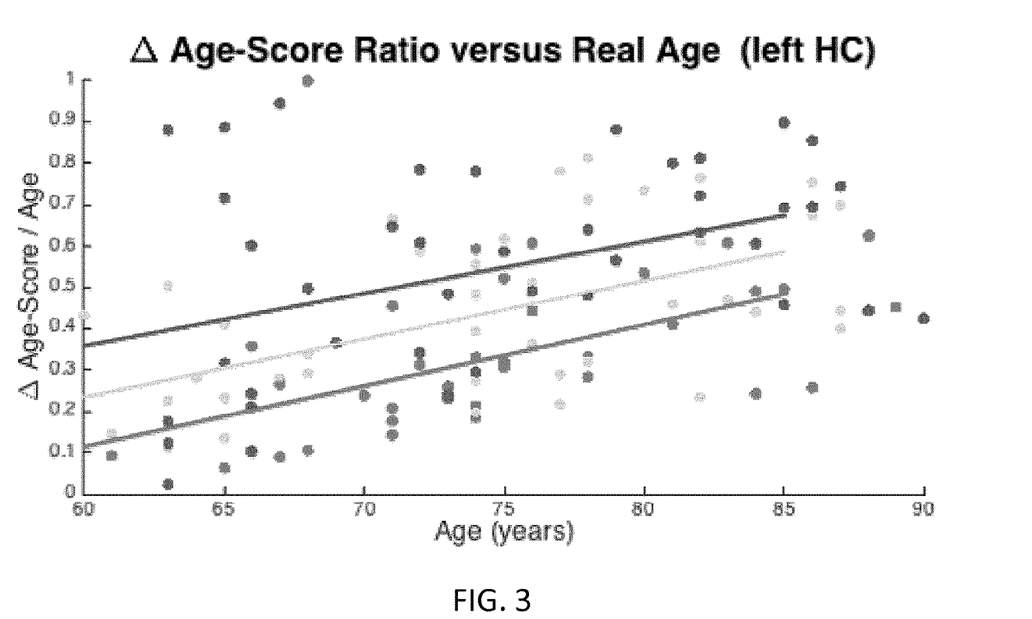
FIG. 3 is a graph showing the difference between estimated hippocampal ages and chronological ages normalized over the chronological ages as a function of the chronological ages.

A second experiment was conducted to exemplify such use of the overall synthetic value. For the purposes of the second experiment, the Applicant analysed released data from the Hippocampus Harmonization project (www.hippocampal-protocol.net), namely images and hippocampal labels for 119 individuals with the best reference model registration, out of the 135 ADNI participants in the Harmonization project (35 CTRL, 41 MCI, 43 AD). The Applicant performed leave-one-out patch-based segmentation and calculated hippocampal ages for all subjects. The reported score was calculated as the weighted sum of all CTRL template subject's chronological ages used by the patch segmentation, over the total sum of the weights from all (CTRL and AD) templates. The delta ($\Delta$) hippocampal age score is the difference between this calculated hippocampal age and chronological age. Shown in FIG. 3 is the delta hippocampal age normalized to the chronological age of the subject. Clearly, AD subjects have an "older" hippocampal age than MCI subjects, who, in turn, have "older" hippocampal age than CTRL subjects. If for a 65-year-old test subject, the value of the delta hippocampal age score normalized to the chronological age is 0.38, a comparison against the graph presented in FIG. 3 could yield a state of health that would reflect a likelihood of AD. If for the same subject, the calculated value is 0.17, the state of health would reflect a likelihood of normal cognitive functions.

Figure 4:
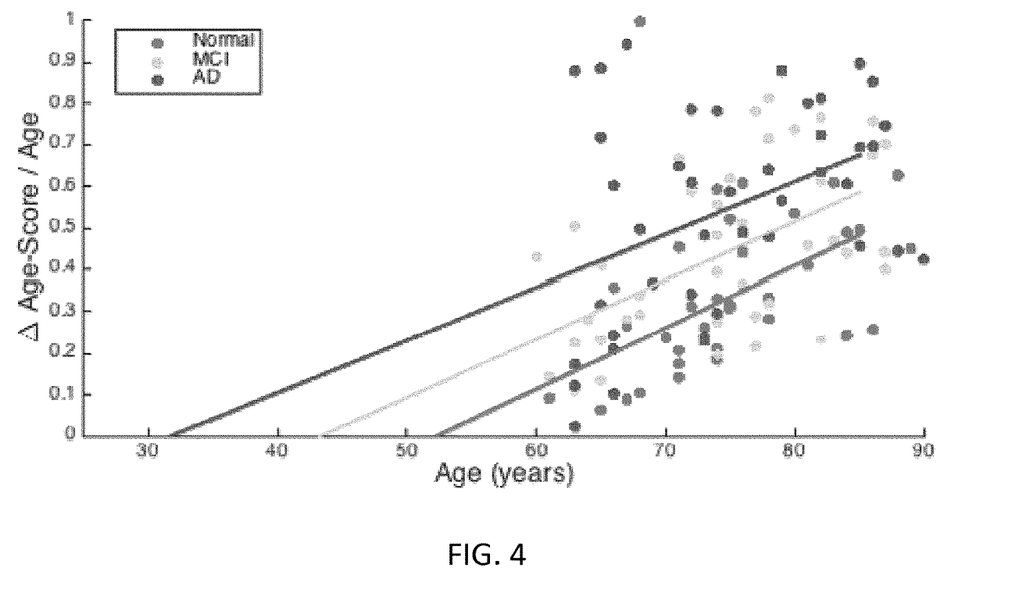
FIG. 4 is a graph generated from an interpolation of the data presented in FIG. 3.

In yet other embodiments, the overall synthetic value can be compared against a known value to assess the difference, or delta, therebetween, for the test subject, and subsequently compare the difference assessed for the test subject against values interpolated from differences assessed for reference subjects presenting different health profiles. This type of interpretation of the overall synthetic value will now be described with reference to FIG. 4, which presents a graph resulting from an interpolation of the values shown in FIG. 3. When interpolating the resulting fits to the x-axis (i.e. the point at which their HC should be completely "normal") the Applicant finds that AD subjects in particular start departing from normality in their mid-30s. Robust fitting provides intercepts (age, standard deviation) as follows: NC: 53 (6.0) years old; MCI 43.3 (7.4) years old; and AD 31.7 (20.6) years old. For a 50-year-old test subject, if the value of the delta hippocampal age score normalized to the chronological age is 0.25, a comparison against the graph presented in FIG. 4 could yield a state of health that would reflect a likelihood of developing AD, whereas if the value is 0.1, the state of health would reflect a likelihood of developing MCI. For AD, the present invention stretches the predictive range to two full decades before clinical diagnosis, which constitutes a significant advance in the field of medical diagnostics, as early detection is critical for treatment success.

While the state of health has been described as derived from the overall synthetic value, it can alternatively be derived from a combination of relevant metrics including the overall synthetic value to improve accuracy. For instance, if the overall synthetic value corresponds to the cortical age of a brain, the combination fo relevant metrics can also include the test subject's known Braak score and blood test results.

Figure 5:
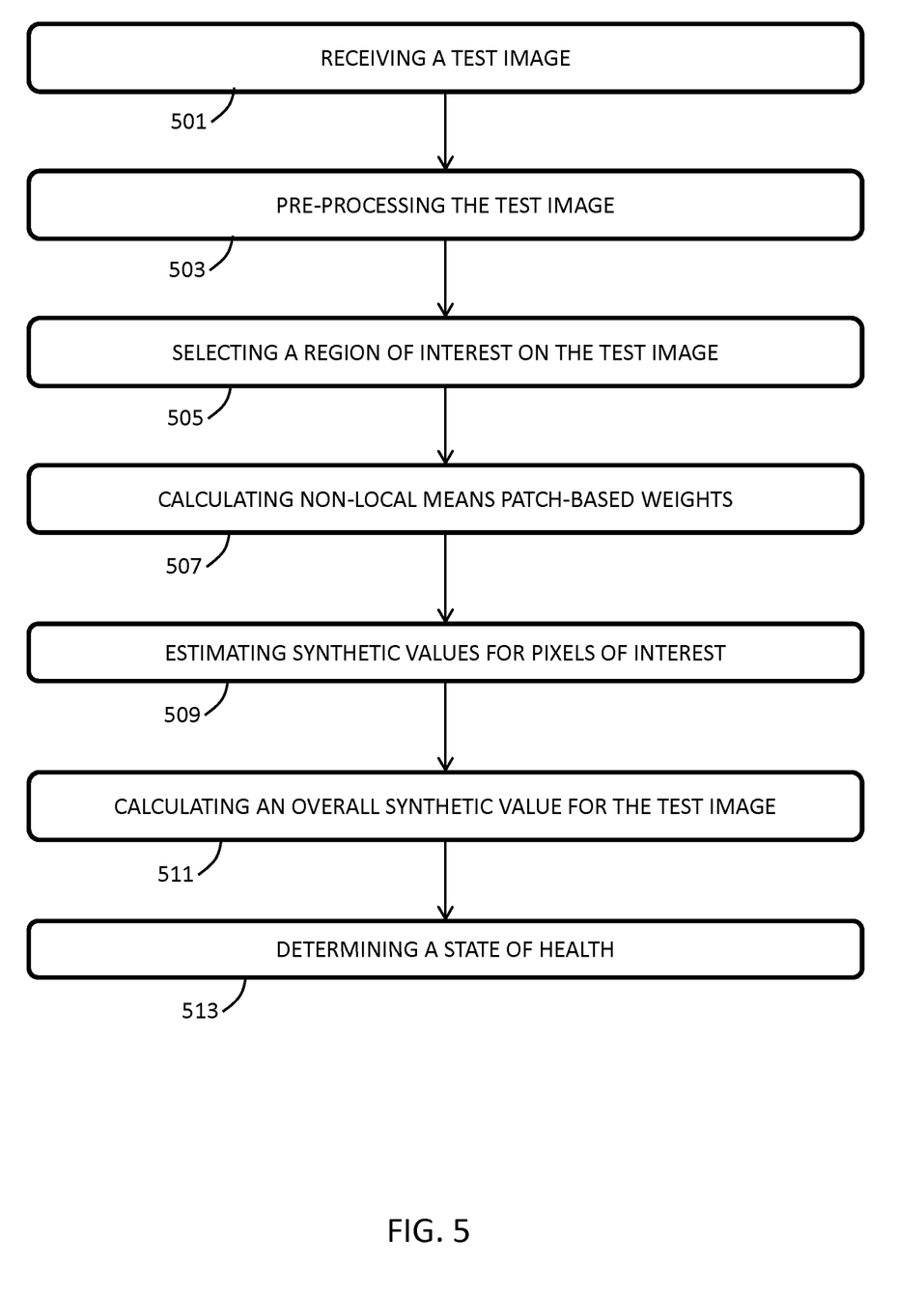
FIG. 5 is a flowchart of the method of the present invention.

Referring now to FIG. 5, there is shown a flowchart of the method of the present invention according to one embodiment of the invention. The method comprises receiving a test image (step 501); pre-processing the test image (step 503); selecting a region of interest on the test image (step 505); calculating non-local means patch-based segmentation mask using the original technique; calculating the refined boundary for the new segmentation mask using the current technique; calculating weights comparing patches surrounding pixels of interest in the test image with a number of patches of pixels surrounding a corresponding number of pixels in reference images (step 507); estimating for the pixels of interest at least one synthetic value of a quantitative metric using a given quantitative metric value assigned to the reference images and the weights (step 509); calculating an overall synthetic value for the test image (step 511); and determining a state of health of the subject as a function of the overall synthetic value (step 513). It will be appreciated that all aspects of the above method can be performed by a computer using software programmed to carry out the described method.

Figure 6:
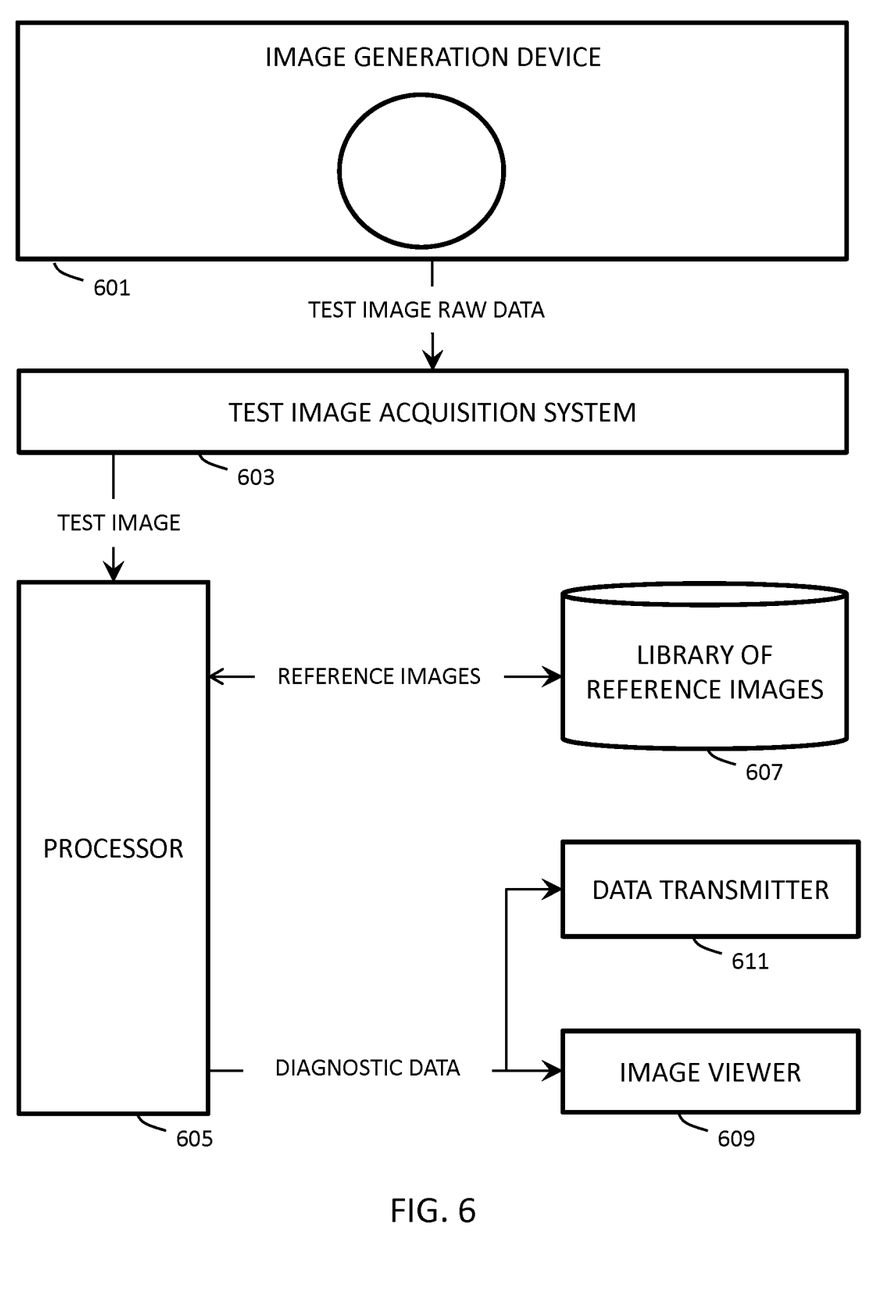
FIG. 6 is a schematic block diagram of the system of the present invention where system components communicate directly with one another.

Referring now to FIG. 6, there is shown a schematic block diagram of the system of the present invention according to a preferred embodiment, where system components communicate directly with one another. In this setup, a test subject is placed inside an image generation device 601 (in this case, an MRI machine) to generate an image of the brain. The imaging is performed by radio frequency emitters/sensors that are placed inside the MRI machine. The RF sensors send data to an image acquisition system 603 for acquiring data that will be used to generate images of the brain. A library of reference images 607 is compared to the test image in the processing step to determine grading and/or volume of a structure for state determination. The image can be pre-processed and processed in a processor 605. After the various processing steps occurring in the processor 605 (shown in more detail in FIG. 8), any diagnostic (or prognostic) data associated with the process and relevant to the patient and healthcare professional such as the test image, the overall synthetic value, and the state of health, are ready to be viewed on an image viewer 609 or transmitted via a data transmitter 611. In some cases, the test image belongs to a test subject for which a medical diagnosis has been reliably obtained. In such cases, the test image can be directly incorporated into the library of reference images 607 or the processor can seed the library of reference images 607 with the images for which the diagnosis is known. The method and apparatus of the present invention rely critically on the reference images in the library of reference images 607 and the greater the number of reference images used in the calculations, the more reliable the estimation of the synthetic values. It is therefore advantageous to increase the number of reference images for which a medical diagnosis is known. One way to achieve this would be to anonymize the test images with a code such that when a patient receives a medical diagnosis, the reference library is automatically updated with the information.

Figure 7:
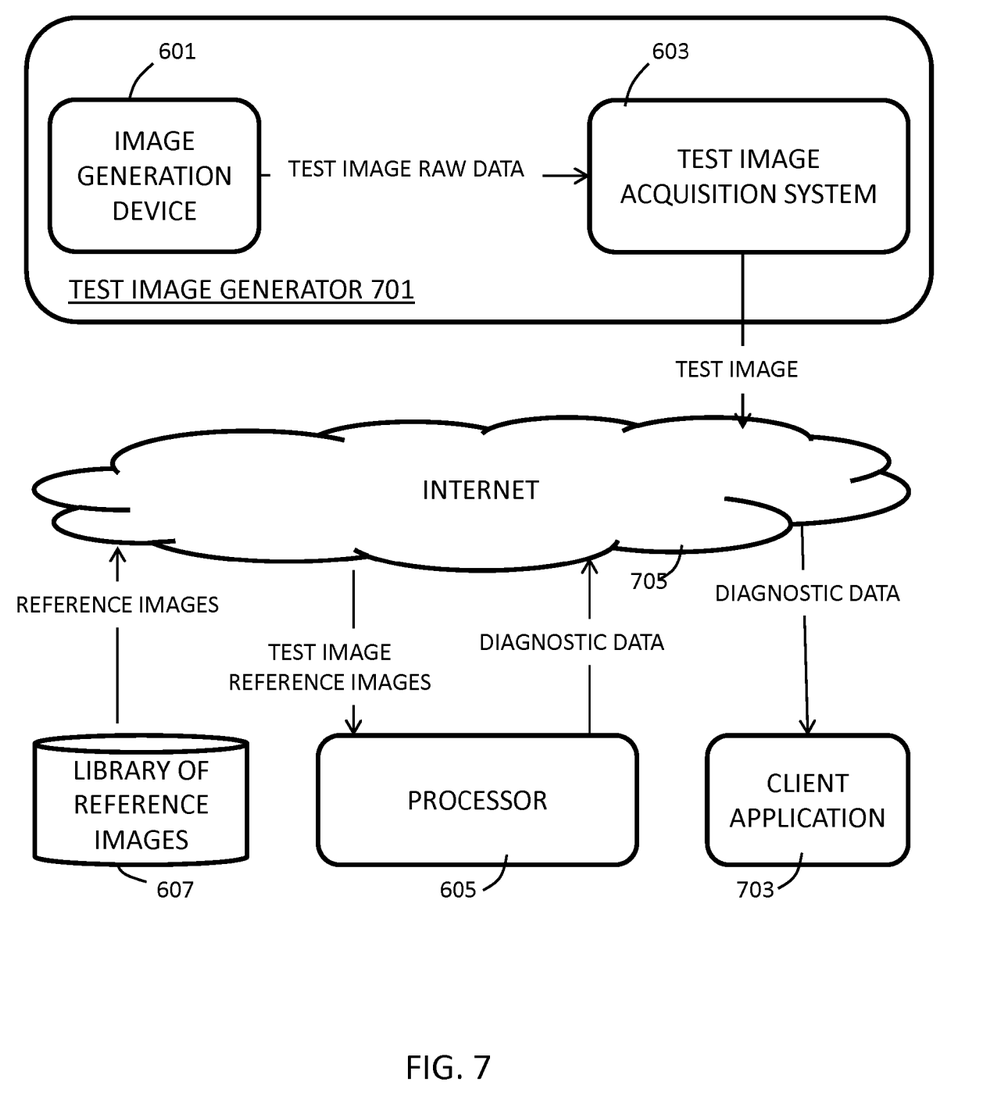
FIG. 7 is a schematic block diagram of the system of the present invention where system components communicate with one another through a computer network.

Referring now to FIG. 7, there is shown a schematic block diagram of the system of the present invention according to a preferred embodiment, where system components communicate with one another through a computer network. A test image generator 701, the processor 605, the library of reference images 607 and a client application 703 are not in a same physical location and communicate with one another through a network 705 such as the Internet. The client application 703 can, for instance, be located at the healthcare professional's office or the test subject's home.

Figure 8:
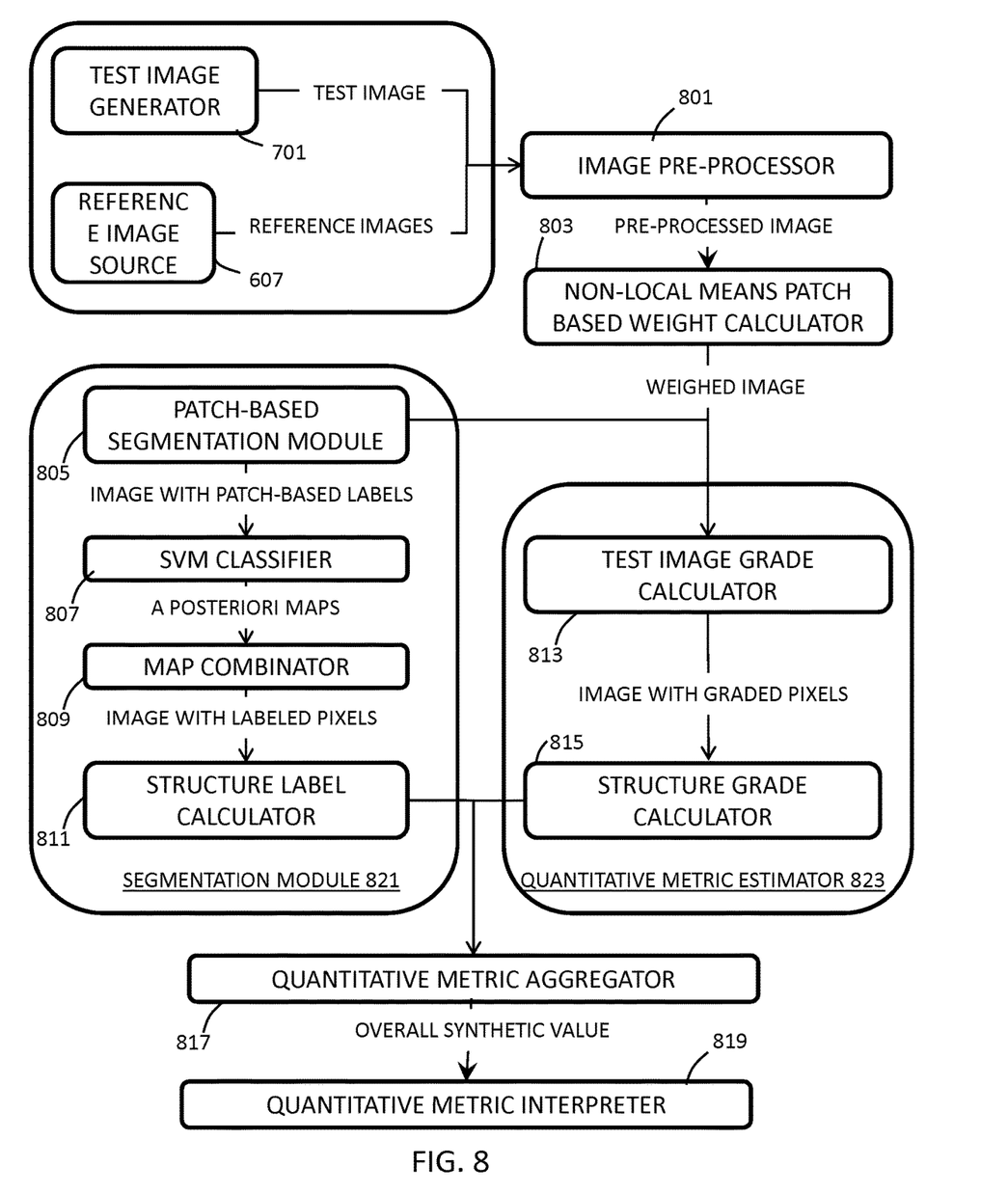
FIG. 8 is a schematic block diagram of the apparatus of the present invention.

Referring now to FIG. 8, there is shown a schematic block diagram of the apparatus 605 of the present invention. An image pre-processor 801 receives and pre-processes a test image and a plurality of reference images. A non-local means patch-based weight calculator 803 generates weighted image data from the pre-processed images and provides the weighted image data to a segmentation module 821 for the purposes of segmentation and to a quantitative metric estimator 823 for the purposes of grading.

Within the segmentation module 821, a patch-based segmentation module 805 generates a test image with patch-based labels for the pixels, an SVM classifier 807 adjusts the labels as a function of local tissue intensity and generates a posteriori maps for the pixels, and a map combinator 809 combines maps generates for each pixel to provide a test image with labeled pixels. A structure label calculator 811 calculates structure-based labels for each structure and provides the test image along with the structure-based labels to a quantitative metric aggregator 817.

Within the quantitative metric module 823, a test image grade calculator 813 estimates synthetic values or grades for the pixels and provides the test image along with the pixel-based synthetic values to a structure grade calculator 815. The structure grade calculator 815 calculates structure-based synthetic values from the pixel-based synthetic values and provides the test image along with the structure-based synthetic values to the quantitative metric aggregator 817.

The quantitative metric aggregator 817 generates an overall synthetic value from the structure-based labels provided by the structure label calculator 811 and the structure-based synthetic values provided by the structure grade calculator 815. A quantitative metric interpreter 819 derives a state of health of the subject from the overall synthetic value, and in some cases, from a combination of the overall synthetic value and other known metric values of the test subject. The state of health can consist in a diagnosis, a prognosis, or both.

It will be appreciated that non-local mean refers to the method of Buades for denoising images presented in Buades et al. [Buades, A., Coll, B., Morel, J. M., 2005. *A non-local algorithm for image denoising*. 2005 IEEE Computer Society Conference on Computer Vision and Pattern Recognition, Vol 2, Proceedings, 60-65.]. Also, while the present invention has been described as involving a patch-based segmentation enhanced through the use of SVM classifiers, it can alternatively perform a patch-based segmentation without any such enhancement or with other enhancements as provided by graph-based procedures or linear regression tools. Furthermore, it will be appreciated that other structures can be used to improve the estimation of synthetic values and the present invention can be applied to other diseases.

It is understood that the term "structure" is not limited to the brain and can be any structure identified in an image. For instance, the structure can correspond to HC, EC, a nucleus, an organ, a muscle, a breast, a blood vessel, a gland, a cartilage, a ligament, or a bone. In some embodiments, the structure can actually be void of any tissue and thus defined by its inner or outer surface. The structure can also be a space filled with a fluid (cerebro-spinal fluid) such the ventricles.

It will be appreciated that throughout this description, the term "state of health" includes a current state of health in some cases, and a predicted state of health in others, depending on the manner in which the synthetic values are interpreted. For segmentation purposes, the term "label" refers to an indication as to whether a pixel belongs to a structure of interest. Labels can have binary values whereas states of health can have values reflecting a continuum from completely healthy to completely diseased. As mentioned previously, it will be appreciated that, in some embodiments, the state of health can be prognostic rather than diagnostic. The method, apparatus, and system of the present invention can be used in longitudinal or multi-modal studies in order to determine, for example, tumor size/growth rate/progression.

It will be appreciated that the term "subject" refers to any person whose image has been processed as per the method, by the apparatus, or by the system of the present invention. The subject can be healthy or diseased. Reference images can be obtained, among others, from a template library, from a collection of pre-labelled datasets, from a collection of datasets from subjects with known quantitative metric values.

Although the specification presents one way of selecting and weighing patches, other methods can be used instead. For example, patch selection and weighting can be based on subject's age, gender or other clinical data such as cognitive scores, genetic phenotype, or other clinical data. It is important to note that averaging a grade (g) within a structure may be sub-optimal for some quantitative metrics or diseases and alternative inter or intra-structural weight distribution schemes (e.g. multi-variate logistic regression) can be used to obtain better results. For instance, the anterior part of HC may prove to be more useful for diagnostic purposes than other parts of HC.

The terms "pixel" and "voxel" are used interchangeably in the specification and the invention works in 2 dimensions (2D), 3 dimensions (3D) and n dimensions using either a single modality or multiple modalities. The image can be multi-dimensional, for example a 2D set of pixels, a 3D set of voxels, a 3D dataset comprising of 2D pixels acquired over time, a 4D dataset of 3D voxels over time, a 4D dataset of 3D voxels where each voxel is represented by a spectrogram. The terms "grade" and "synthetic values" are used interchangeably in the specification.

The term "network" should be understood as including internal networks, the Internet and any displacement of any type of physical media such as CDs and flash memory from one place to another. The term "image" in the present invention refers to any image such as an image generated in a magnetic resonance imaging (MRI), positron-emission tomography (PET), computerized tomography (CT), fluoroscopy, X-ray, etc. The term "pre-processing" refers to at least one of image format conversion, denoising, regridding, correction of intensity inhomogeneity, registration to a library image, isotropic resampling, intensity clamping, intensity standardization, and non-linear alignment.

Among the advantages of the present invention for medical professionals are increasing productivity, increasing confidence in diagnosis, increasing confidence in treatment plans, leveraging state-of-the-art knowledge, enabling personalized medicine, allowing to predict if a patient will benefit from a particular drug. Among the advantages of the present invention for pharmaceutical companies are allowing to determine if a patient will benefit from a particular drug, using the present invention as a selection and an enrichment tool for clinical trials, such as decreasing sample size or targeting responders.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

What is claimed is:

1. An apparatus for processing medical images including a test image initially segmented to provide a segmentation mask having boundaries comprising pixels/voxels of interest, comprising:
   a processor;
   memory comprising program code that, when executed by said processor, cause said processor to:
   calculate classifier-driven boundaries on said segmentation mask in said test image and to reassign classes of said pixels/voxels of interest as a function of local tissue intensity using a classifier to produce label values for each one of said pixels/voxels of interest, and generate an a posteriori map;
   estimate, for pixels/voxels of said a posteriori map of said test image, at least one synthetic value of a quantitative metric as a function of said label values using a given value of said quantitative metric assigned to reference images.

2. The apparatus as claimed in claim 1, wherein said memory further comprises program code that, when executed by said processor, further cause said processor to calculate an overall synthetic value for said test image from said at least one synthetic value.

3. The apparatus as claimed in claim 2, wherein said memory further comprises program code that, when executed by said processor, further cause said processor to calculate a mean value of said at least one synthetic value, and said overall synthetic value is said mean value.

4. The apparatus as claimed in claim 2, wherein said memory further comprises program code that, when executed by said processor, further cause said processor to determine a state of health from said overall synthetic value.

5. The apparatus as claimed in claim 4, wherein said memory further comprises program code that, when executed by said processor, further cause said processor to compare said overall synthetic value against a predetermined scale specific to said quantitative metric in determining said state of health.

6. The apparatus as claimed in claim 4, wherein said memory further comprises program code that, when executed by said processor, further cause said processor to compare the difference between said overall synthetic value and a real value associated with said test image against a predetermined scale specific to the difference between synthetic and real values for said quantitative metric in determining said state of health.

7. The apparatus as claimed in claim 1, wherein said quantitative metric is the cortical age of a brain.

8. The apparatus as claimed in claim 1, wherein said classifier is a support vector machine classifier.

9. The apparatus as claimed in claim 8, wherein said classifier comprises assigning for each one of said pixels/voxels of interest a vector of predictors of length N using the formula:

$$X_k = [\mu_k \sigma_k \tilde{\mu}_k^3 \tilde{\mu}_k^4 \tilde{\mu}_k^5 |\nabla I|_k \nabla^2 I_k \nabla_{9 4}^2 I_k]$$

wherein:

$\mu_k$ and $\sigma_k$ are the local mean and standard deviation of the intensity in a neighbourhood centered at pixel/voxel k, $$\tilde{\mu}_k^n = \frac{1}{27} \sum_{i=1}^{27} \left( \frac{I_i - \mu_k}{\sigma_k} \right)^n$$

$I_l$ are the pixel/voxel intensities in said neighbourhood, $|\nabla I|_k$ is the norm of the local intensity gradient, $\nabla^2 I_k$ is a Laplacian kernel, and $\nabla_o^2 I_k$ is a Laplacian of a Gaussian kernel.

10. The apparatus as claimed in claim 9, wherein said classifying further comprises calculating said label values using a formula:

$$v(x_i) = \frac{\sum_{s=1}^{N} \sum_{j \in \Omega} w(x_i, x_{s,j}) \cdot l(x_{s,j})}{\sum_{s=1}^{N} \sum_{j \in \Omega} w(x_i, x_{s,j})}$$

where l is a label (0 for non-structure and 1 for structure), w is a weight, xi is the pixel/voxel of interest of the test image, xs,j is a pixel/voxel in a reference image, Ω is a set of all said pixels/voxels of interest and a pixel/voxel v(xi) is segmented as structure when v(xi) is greater than 0.5.

11. The apparatus as claimed in claim 1, wherein said pixels/voxels of interest define a region of interest of said test image, said region of interest comprising a structure that changes with said quantitative metric.

12. The apparatus as claimed in claim 11, wherein said memory further comprises program code that, when executed by said processor, further cause said processor to isolate said region of interest from said test image.

13. The apparatus of claim 11, wherein said structure comprises one or more of a left hippocampus, a right hippocampus, a left entorhinal cortex, and a right entorhinal cortex.

14. The apparatus as claimed in claim 1, wherein a reference patch used in said calculating is selected according to its relatedness to a test patch surrounding said pixels/voxels of interest.

15. The apparatus as claimed in claim 14, wherein said relatedness is determined by a mean and a standard deviation of intensity values of said test patch pixels/voxels and said reference patch pixels/voxels.

16. The apparatus as claimed in claim 1, wherein said estimating further comprises estimating at least one synthetic value using the formula:

$$g(x_i) = \frac{\sum_{s=1}^{N} \sum_{j \in \Omega} w(x_i, x_{s,j}) \cdot p_s}{\sum_{s=1}^{N} \sum_{j \in \Omega} w(x_i, x_{s,j})}$$

where:

$$w(x_i, x_j) = e^{\frac{-\|P(x_i) - P(x_j)\|_2^2}{h^2}}$$

and g(xi) is a grade, N is a number of subjects, w is a weight, $p_s$ is said given value of said quantitative metric, P is a patch surrounding a pixel/voxel, $x_i$ is the pixel/voxel of interest of the test image, $x_i$ and $x_{s,j}$ are a pixel/voxel in a reference image, Ω is a set of all said pixels/voxels of interest and $h^2$ is a smoothing function.

17. The apparatus of claim 1, wherein a patch size of said pixels/voxels of interest is between 1×1×1 voxels and 100×100×100 voxels.

18. A system for processing medical images comprising:
a medical imager for generating a test image;
an apparatus for processing medical images comprising:
a processor; and
memory storing program code that, when executed by said processor, cause said processor to:
calculate classifier-driven boundaries on a segmentation mask in said test image and to reassign classes of pixels/voxels of interest as a function of local tissue intensity using a classifier to produce label values for each one of said pixels/voxels of interest, and generate an a posteriori map; and
estimate, for said pixels/voxels of said a posteriori map of said test image, at least one estimation of a synthetic value of a quantitative metric as a function of said label values using a given value of said quantitative metric assigned to said reference images;
a client application configured to receive and present data provided by said apparatus;
wherein said imager, apparatus, and client application communicate data over a network and return to said client application said overall synthetic value.

19. The system as claimed in claim 18 wherein said medical imager is an MRI scanner.

20. A computing device for processing medical images including a test image initially segmented to provide a segmentation mask having boundaries comprising pixels/voxels of interest, comprising:
a processor that is configured to implement:
calculating classifier-driven boundaries on said segmentation mask in said test image and reassigning classes of said pixels/voxels of interest as a function of local tissue intensity using a classifier to produce label values for each one of said pixels/voxels of interest, and generating an a posteriori map; and
estimating, for pixels/voxels of said a posteriori map of said test image, at least one synthetic value of a quantitative metric as a function of said label values using a given value of said quantitative metric assigned to reference images.

* * * * *